(12) United States Patent
Zimmerling et al.

(10) Patent No.: US 9,474,537 B2
(45) Date of Patent: Oct. 25, 2016

(54) SURGICAL TOOL FOR IMPLANTATION OF A DEVICE WITH A CONVEX ELEMENT

(75) Inventors: Martin Zimmerling, Patsch (AT); Bernhard Jamnig, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1487 days.

(21) Appl. No.: 12/350,550

(22) Filed: Jan. 8, 2009

(65) Prior Publication Data

US 2009/0177220 A1    Jul. 9, 2009

Related U.S. Application Data

(60) Provisional application No. 61/019,689, filed on Jan. 8, 2008.

(51) Int. Cl.
| | |
|---|---|
| A61B 17/00 | (2006.01) |
| A61B 17/17 | (2006.01) |
| A61B 17/02 | (2006.01) |
| A61B 17/16 | (2006.01) |
| A61N 1/05 | (2006.01) |
| A61N 1/36 | (2006.01) |

(52) U.S. Cl.
CPC ........... *A61B 17/1739* (2013.01); *A61B 17/02* (2013.01); *A61B 17/0218* (2013.01); *A61B 17/1679* (2013.01); *A61B 17/17* (2013.01); *A61B 2017/1771* (2013.01); *A61N 1/0541* (2013.01); *A61N 1/36032* (2013.01)

(58) Field of Classification Search
CPC .............. A61B 17/02; A61B 17/0218; A61B 17/0281; A61B 17/17; A61B 17/1739; A61B 2017/0212; A61B 2017/1771
USPC ....... 600/201, 203, 206, 208, 210, 215, 226, 600/235, 238, 237, 241, 242; 606/90, 191, 606/198, 86 R, 96–98
See application file for complete search history.

(56) References Cited

U.S. PATENT DOCUMENTS

| | | | | |
|---|---|---|---|---|
| 770,854 | A * | 9/1904 | Hare | 600/238 |
| 1,217,745 | A * | 2/1917 | Gracey | 600/222 |
| 5,074,847 | A * | 12/1991 | Greenwell et al. | 604/174 |
| 5,868,745 | A * | 2/1999 | Alleyne | 606/86 R |
| 6,308,101 | B1 | 10/2001 | Faltys et al. | 607/57 |
| 6,428,474 | B1 * | 8/2002 | Weiss | 600/224 |
| 8,696,560 | B2 * | 4/2014 | Strauss et al. | 600/219 |

(Continued)

FOREIGN PATENT DOCUMENTS

WO    WO 03/092326 A1    11/2003    ............. H04R 25/00

OTHER PUBLICATIONS

European Patent Office, International Search Report, Jan. 27, 2009, PCT/US2008/079270.

*Primary Examiner* — Kevin T Truong
*Assistant Examiner* — Tracy Kamikawa
(74) *Attorney, Agent, or Firm* — Sunstein Kann Murphy & Timbers LLP

(57) ABSTRACT

A surgical tool lifts an overlying layer of skin away from underlying bone to prepare the bone to accommodate a convex element of an implantable device. The tool includes a lifting shell for insertion between the skin and the bone so as to lift the skin away from bone. A tool base supports the lifting shell and is supported by the bone. A drill template opening in the tool base provides access for preparing the bone to accommodate the convex element.

18 Claims, 5 Drawing Sheets

(56) References Cited

U.S. PATENT DOCUMENTS

| | | | |
|---|---|---|---|
| 2003/0171787 A1 | 9/2003 | Money et al. | 607/57 |
| 2004/0167529 A1* | 8/2004 | Papendick et al. | 606/86 |
| 2004/0243177 A1 | 12/2004 | Svehla et al. | 606/210 |
| 2005/0004629 A1 | 1/2005 | Gibson et al. | 607/60 |
| 2005/0245960 A1* | 11/2005 | Grundeman | 606/192 |
| 2006/0155169 A1* | 7/2006 | Bastia | A61B 1/00105 600/199 |
| 2006/0287583 A1* | 12/2006 | Mangiardi | 600/208 |
| 2008/0221641 A1 | 9/2008 | Hochmair et al. | 607/57 |
| 2009/0099403 A1 | 4/2009 | Zimmerling et al. | 600/12 |

* cited by examiner

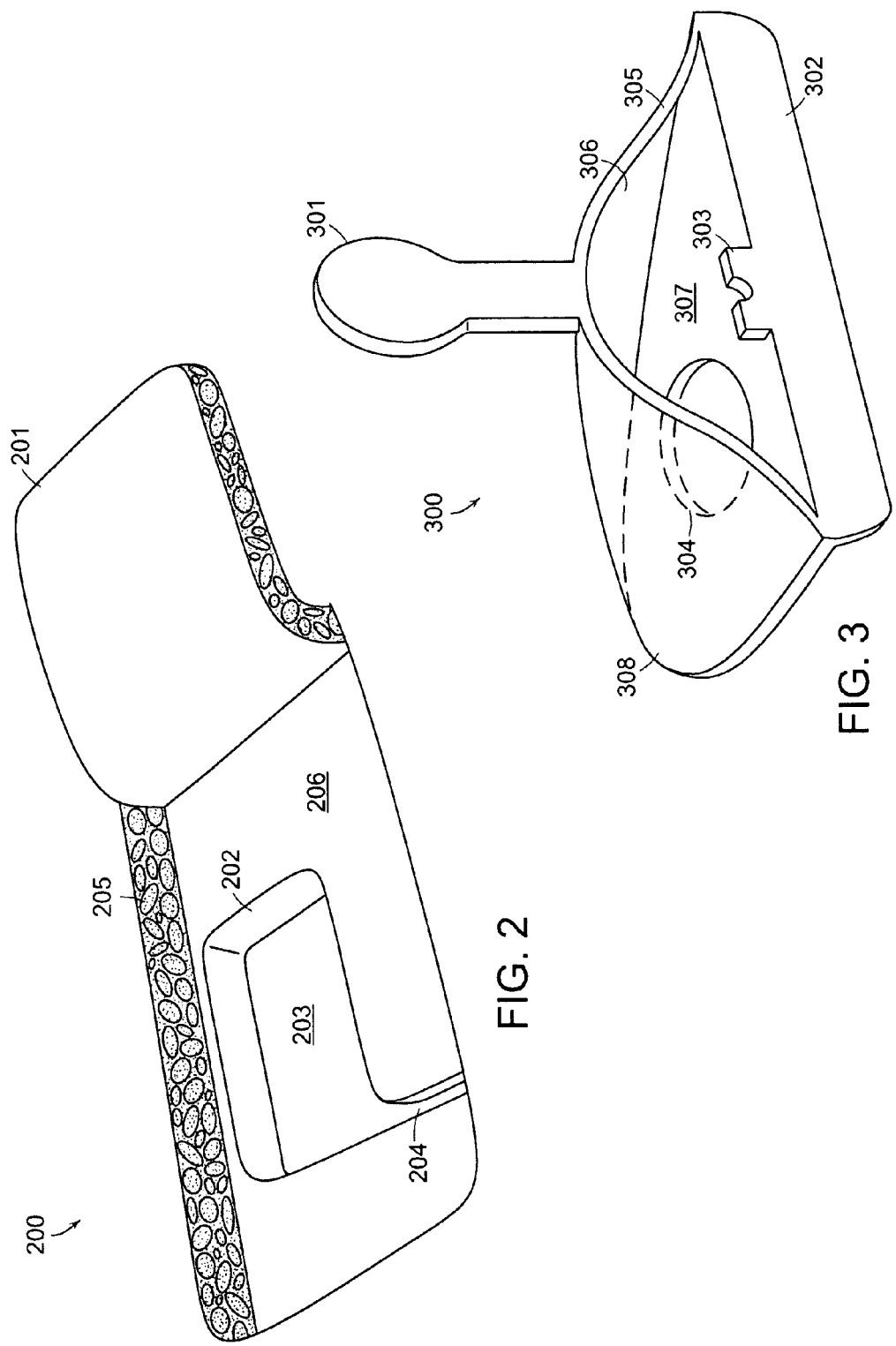

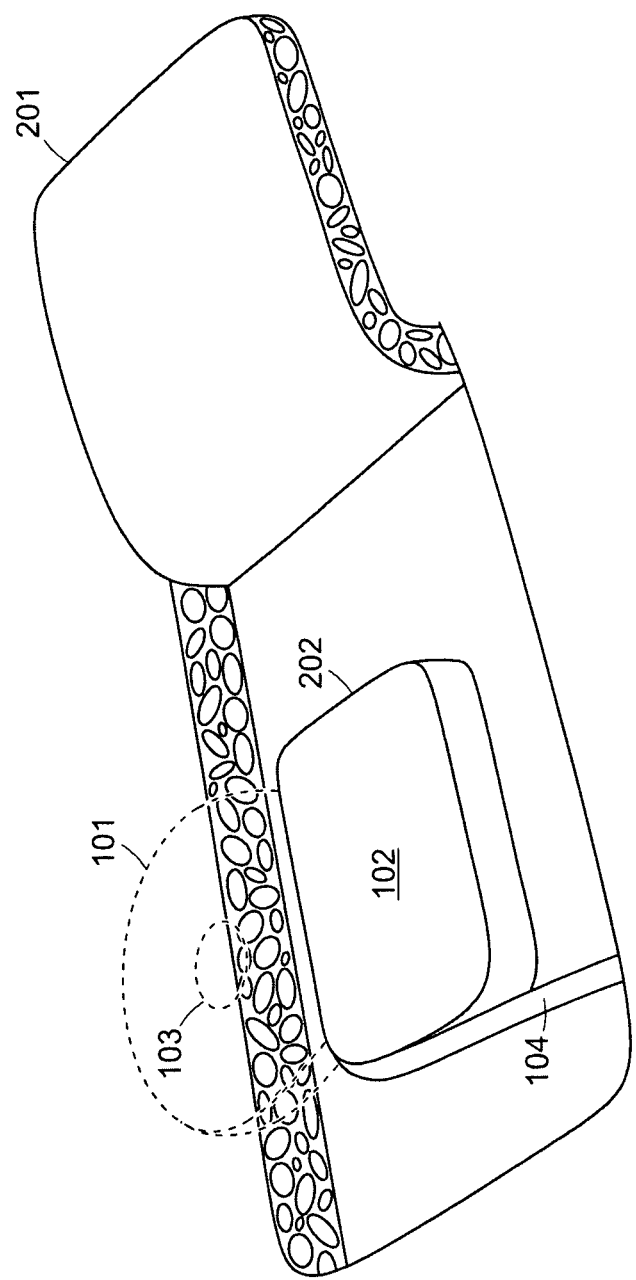

SURGICAL TOOL FOR IMPLANTATION OF A DEVICE WITH A CONVEX ELEMENT

This application claims priority from U.S. Provisional Patent Application 61/019,689, filed Jan. 8, 2008, which is incorporated herein by reference.

FIELD OF THE INVENTION

The present invention relates to surgical tools, and more specifically to a surgical tool for implanting a device with a convex element.

BACKGROUND ART

We have entered an age in which various medical conditions are treatable based on implantation inside a patient of a special device or system. For example, cochlear implants are electronic systems designed to provide useful hearing and improved communication ability to individuals who are profoundly hearing impaired and unable to achieve speech understanding with conventional hearing aids. A typical system includes an implantable stimulator containing electronic circuitry, a coil for power and information transfer, and a stimulation electrode array which is inserted into the inner ear (and perhaps a counter electrode).

FIG. 1A shows a side view and FIG. 1B shows an elevated bottom perspective view of one specific example of an implantable device 100 having a convex element, in this case, a portion of a cochlear implant system. The implantable device 100 includes a coil housing 101 containing receiving coils for receiving a power and/or data signal from an external transmitting coil (not shown). Attached to the coil housing 101 is a stimulator housing 102, which in the case of a cochlear implant system contains modules for developing an electrode stimulation signal for stimulating cochlear nerve tissue. Centered within the coil housing 101 is a convex element 103, which in the case of a cochlear implant system would typically be a magnet housing containing a positioning magnet that coordinates with a corresponding magnetic element in the external transmitting coil arrangement to hold it in a proper operating position for transferring the signal across the skin into the receiving coils. Also connected to the stimulator housing 102 as an electrode lead 104 which in the case of a cochlear implant system connects to an electrode array (not shown) that applies the stimulation signal to the cochlear nerve tissue.

Currently, a surgeon implanting a device with a convex element uses a surgical spreader device to lift a skin flap including the periosteum and then determine and mark the location to provide a recess in the bone structure to accommodate the convex element. Once the location is marked, a drill can be used to drill a recess into the bone at the marked location.

SUMMARY OF THE INVENTION

Embodiments of the present invention are directed to a surgical tool that lifts an overlying layer of skin away from underlying bone to prepare the bone to accommodate a convex element of an implantable device. The tool includes a lifting shell for insertion between the skin and the bone so as to lift the skin away from bone. A tool base supports the lifting shell and is supported by the bone. A drill template opening in the tool base provides access to prepare the bone to accommodate the convex element.

In further specific embodiments, the surgical tool includes a gripping handle for a surgeon to push on the tool for insertion between the skin and the bone. The tool may also include a stopper bar attached perpendicularly to the tool base for limiting how far the tool may be inserted. And there may be a shaft guide atop the stopper bar with a center recess for receiving a drill shaft used for preparing the bone.

In specific embodiments, preparing the bone includes creating a recess in the bone to accommodate the convex element. For example, the recess may be created by a spherical burring end of a drill.

The implantable device may specifically be part of a cochlear implant system. For example, the convex element may be a magnet housing of the cochlear implant system.

BRIEF DESCRIPTION OF THE DRAWINGS

FIG. 2 shows an example of a typical implant site which has been prepared for surgical implantation of an implantable device.

FIG. 3 shows an example of a surgical tool for implantation of a device with a convex element.

FIG. 6 shows placement of the implanted device place in the completed site.

DETAILED DESCRIPTION OF SPECIFIC EMBODIMENTS

Figure 1A:
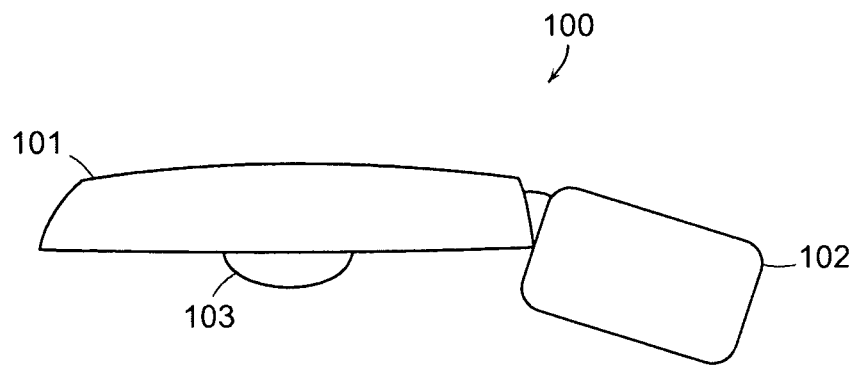
FIG. 1A shows a side view and FIG. 1B shows an elevated bottom perspective view of one specific example of an implantable device having a convex element.
Figure 1B:
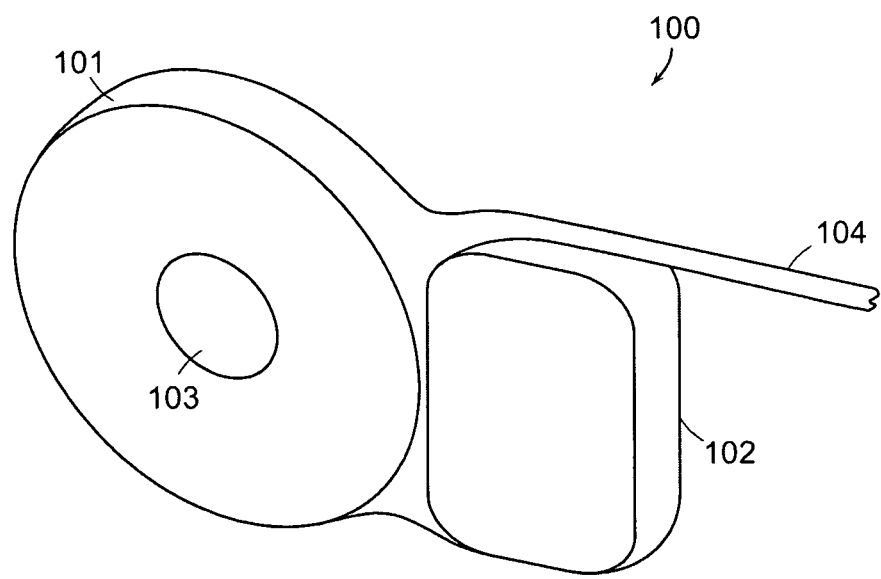

FIG. 2 shows an example of a typical implant site 200 which has been prepared for surgical implantation of an implantable device 100. A skin flap 201 including the periosteum has been incised in the patient's skin 205 and lifted back from the underlying bone 206. A housing recess 202 is created in the underlying bone 206 down to some predetermined depth so as to form a bone bed 203 at the bottom of the housing recess 202. Optionally, an electrode channel 204 may also be prepared to receive a portion of the electrode lead 104.

FIG. 3 shows an example of a surgical tool 300 for implantation of a device with a convex element. At the top is a gripping handle 301 held by the surgeon. Opposite to the handle 301 is a stopper bar 302 (1-2 mm in height), with a tool opening 306 defined between them by a bell-shaped lifter shell 305. The lifter shell 305 tapers down and away from the tool opening 306 until it meets the tool base 307 so as to define an insertion edge 308. Underneath the lifter shell 305, the tool base 307 includes a drill template opening 304 which is located the proper distance in from the tool opening 306 and the edge of the stopper bar 302 so as to correspond to a recess needs to be prepared to receive the convex element 103. Also, at the top of the stopper bar 302 is a shaft guide 303 with a center recess for receiving a drill shaft that creates the recess for the convex element 103.

Figure 4:
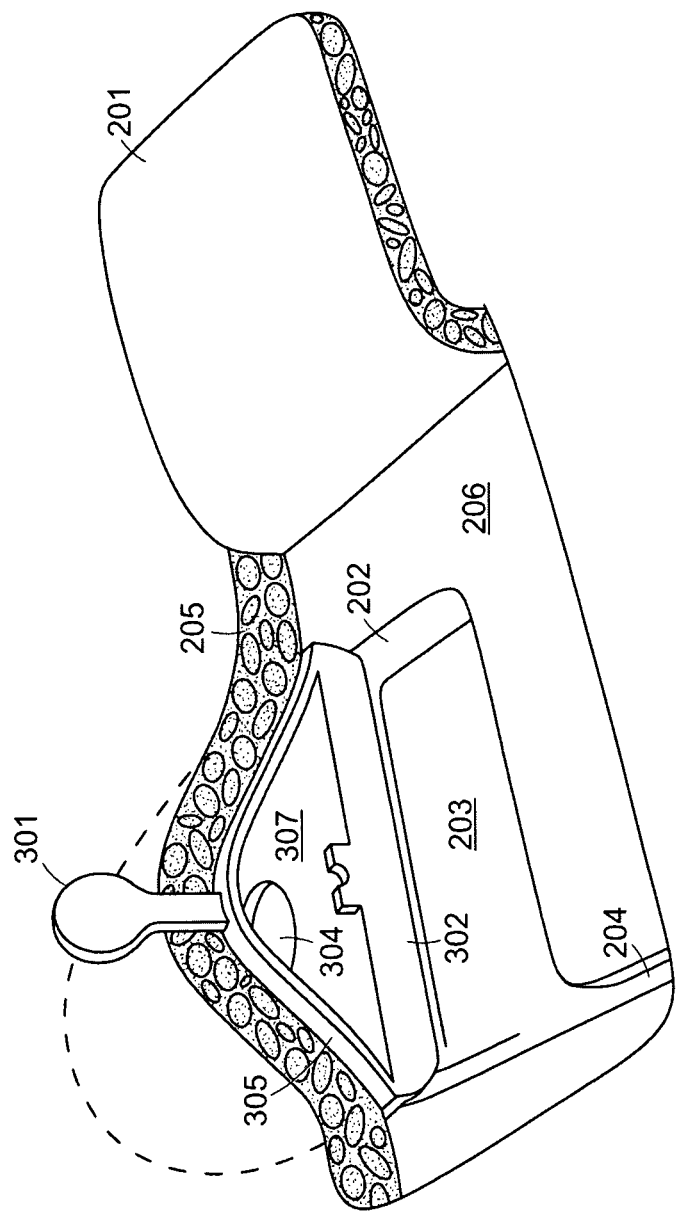
FIG. 4 shows how the surgical tool is inserted.

FIG. 4 shows how the surgical tool 300 is inserted. The surgeon does not need to lift the skin flap with a separate spreader, but holding the tool by its handle 301 the insertion edge 308 is pushed between the patient's skin 205 and the underlying bone 206. This causes the bell-shape of the lifting shell 305 to lift the patient's skin 205 up and away from the underlying bone 206. Insertion of the tool 300 is stopped by the stopper bar 302 engaging the side wall of the housing recess 202. With the insertion tool 300 thus inserted, the drill template opening 304 is then in proper position over the underlying bone 206 with respect to the housing recess 202.

Figure 5:
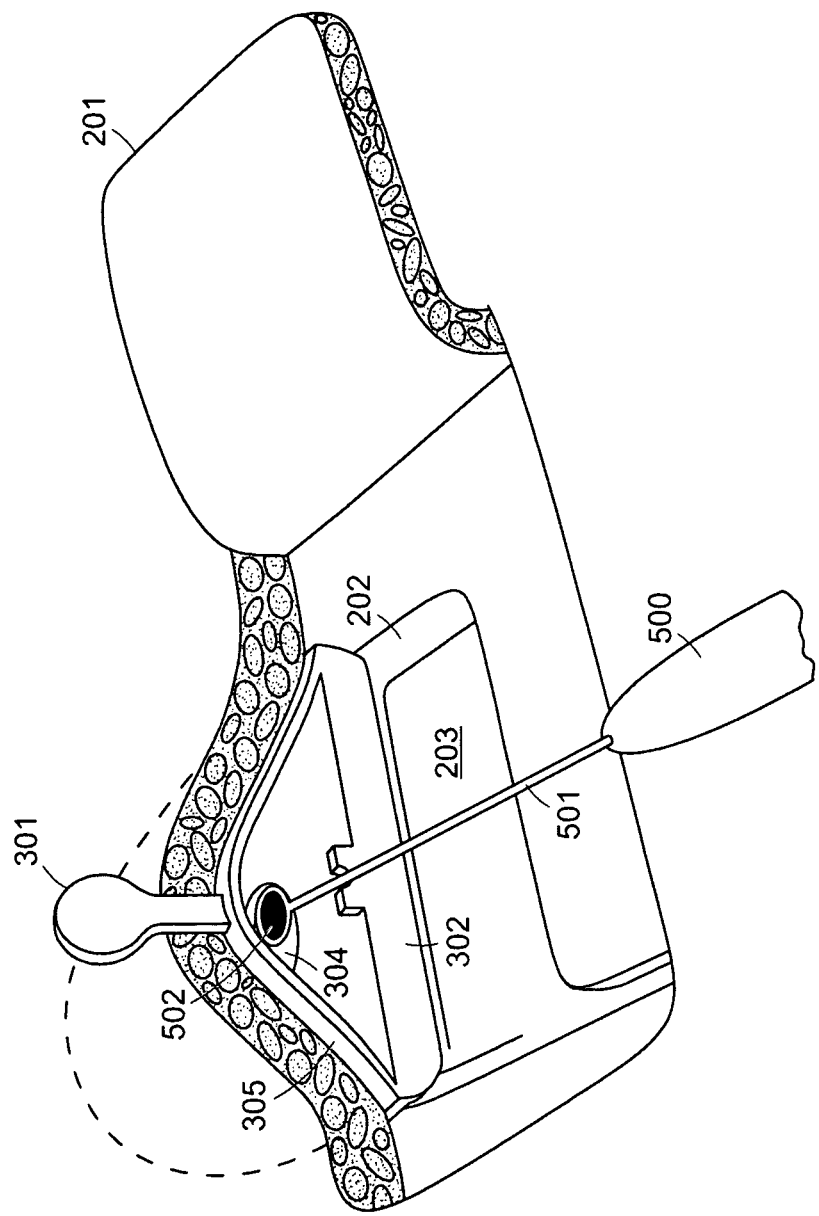
FIG. 5 shows use of a drill to create a recess for the convex element using the surgical tool.

Once the insertion tool 300 has been inserted into proper position, a surgical drill 500 is used with a drill shaft 501 driving spherical burring end 502 at the drill template opening 304, as shown in FIG. 5. This creates a recess for the convex element 103, and, as shown in FIG. 6, the coil housing 101 and its convex element 103 are then slipped into place as well as the stimulator housing 102 into its corresponding housing recess 202 and the electrode lead 104 into the electrode channel 204. Once the remainder of the surgery is complete, the skin flap 201 and periosteum can be returned back into place and stitches made in the incision.

By correctly selecting a proper diameter of the spherical burring end 502 and thickness of the drill shaft 501, only a small incision is needed in order to create a recess for a convex element 103 of an implantable device 100 which is at the correct location and has the correct size and shape. When the surgeon drills the recess into the underlying bone 206 there is less risk of inadvertently damaging the skin flap 201 and periosteum with the drill 500. In addition, the skin flap 201 and periosteum are stretched out only to the minimum extent possible so that there is less risk of overstretching and loss of elasticity and tonicity in the skin flap 201 and periosteum.

Although various exemplary embodiments of the invention have been disclosed, it should be apparent to those skilled in the art that various changes and modifications can be made which will achieve some of the advantages of the invention without departing from the true scope of the invention.

What is claimed is:

1. A surgical tool for lifting an overlying layer of skin away from underlying bone to prepare the bone to accommodate a convex element of an implantable device, the tool comprising:
   a lifting shell having an insertion edge adapted to be pushed between the skin and the bone during insertion, and an opening edge;
   a tool base having an opening edge, a top surface and a bottom surface, the bottom surface configured to lie against the underlying bone and the tool base opening edge formed adjacent to a portion of the top surface, the tool base and the lifting shell connected to one another along the insertion edge so as to form a pocket between the top surface of the tool base and the lifting shell, the lifting shell opening edge and the tool base opening edge forming a tool opening that allows access to an interior area of the pocket, wherein the lifting shell forms a bell-shaped curve near the lifting shell opening edge that tapers down to the insertion edge at two sides, and the lifting shell and the tool base bound the tool opening at the two sides; and
   a drill template opening in the tool base positioned between the insertion edge and the tool base opening edge, the tool base fully surrounding the drill template opening and the bottom surface of the tool base configured to be substantially flat, including around the drill template opening.

2. The tool according to claim 1, further comprising:
   a gripping handle attached to the lifting shell opening edge near its top.

3. The tool according to claim 2, further comprising:
   a stopper bar attached perpendicularly to the tool base opening edge and positioned on an opposite side of the tool opening than the gripping handle, the stopper bar adapted to limit how far the tool may be inserted between the skin and the bone.

4. The tool according to claim 1, further comprising:
   a stopper bar attached perpendicularly to, and extending downwardly from, the tool base opening edge and adapted to limit how far the tool may be inserted between the skin and the bone.

5. The tool according to claim 1, wherein the interior area of the pocket is substantially constant during insertion.

6. The tool according to claim 1, wherein the drill template opening is circular in shape.

7. The tool according to claim 1, wherein the insertion edge forms a u-shape.

8. The tool according to claim 1, wherein the pocket formed between the lifting shell and the top surface of the tool base is enclosed with access to the interior area only through the tool opening and the drill template opening.

9. A surgical tool for lifting an overlying layer of skin away from underlying bone to prepare the bone to accommodate a convex element of an implantable device, the tool comprising:
   insertion means having an insertion edge that is u-shaped for inserting the tool between the skin and the bone;
   supporting means for supporting the insertion means, the supporting means being shaped so as to provide a bottom surface that is configured to lie against the underlying bone, and a top surface, the insertion means and the supporting means connected to one another along the insertion edge and spaced apart from one another at a tool opening so as to form a pocket between the top surface of the supporting means and the insertion means, wherein the insertion means forms a bell-shaped curve near the tool opening that tapers down to the insertion edge at two sides, and the insertion means and the supporting means bound the tool opening at the two sides; and
   access means in the supporting means for providing access to prepare the bone to accommodate the convex element, the supporting means fully surrounding the access means and the bottom surface of the supporting means configured to be substantially flat, including around the access means.

10. The tool according to claim 9, further comprising:
    gripping means for a surgeon to push on the tool for insertion between the skin and the bone, the gripping means attached to the insertion means near a top of the tool opening.

11. The tool according to claim 10, further comprising:
    stopping means attached perpendicularly to the supporting means at the tool opening, and positioned on an opposite side of the tool opening than the gripping means, for limiting how far the tool may be inserted.

12. The tool according to claim 9, further comprising:
    stopping means attached perpendicularly to, and extending downwardly from, the supporting means at the tool opening for limiting how far the tool may be inserted.

13. The tool according to claim 12, further comprising:
    shaft guide means atop the stopping means for receiving drilling means for preparing the bone.

14. The tool according to claim 9, wherein the insertion means and the supporting means form a substantially constant area within the pocket between the insertion means and the supporting means during insertion.

15. The tool according to claim 9, wherein the access means is circular in shape.

16. A surgical tool for lifting an overlying layer of skin away from underlying bone to prepare the bone to accommodate a convex element of an implantable device, the tool comprising:
- a lifting shell having an insertion edge adapted to be pushed between the skin and the bone, and an opening edge;
- a tool base having an opening edge, the tool base and the lifting shell connected to one another along the insertion edge so as to form a pocket between the tool base and the lifting shell, the lifting shell opening edge and the tool base opening edge forming a tool opening that allows access to an interior area of the pocket;
- a drill template opening in the tool base positioned between the insertion edge and the tool base opening edge, the tool base fully surrounding the drill template opening;
- a stopper bar attached perpendicularly to the tool base opening edge and adapted to limit how far the tool may be inserted between the skin and the bone; and
- a shaft guide atop the stopper bar with a center recess adapted to receive a drill shaft used for preparing the bone.

17. A kit comprising:
a surgical tool for lifting an overlying layer of skin away from underlying bone to prepare the bone to accommodate a convex element of an implantable device, the tool comprising:
- a lifting shell having an insertion edge adapted to be pushed between the skin and the bone during insertion, and an opening edge;
- a tool base having an opening edge, a top surface and a bottom surface, the bottom surface configured to lie against the underlying bone and the tool base opening edge formed adjacent to a portion of the top surface, the tool base and the lifting shell connected to one another along the insertion edge so as to form a pocket between the top surface of the tool base and the lifting shell, the lifting shell opening edge and the tool base opening edge forming a tool opening that allows access to an interior area of the pocket, wherein the lifting shell forms a shape near the lifting shell opening edge that tapers down to the insertion edge at two sides, and the lifting shell and the tool base bound the tool opening at the two sides; and
- a drill template opening in the tool base positioned between the insertion edge and the tool base opening edge, the tool base fully surrounding the drill template opening; and a cochlear implant system having the convex element.

18. A kit comprising:
a surgical tool for lifting an overlaying layer of skin away from underlying bone to prepare the bone to accommodate a convex element of an implantable device, the tool comprising:
- insertion means having an insertion edge that is u-shaped for inserting the tool between the skin and the bone;
- supporting means for supporting the insertion means, the supporting means being shaped so as to provide a bottom surface that is configured to lie against the underlying bone, and a top surface, the insertion means and the supporting means connected to one another along the insertion edge and spaced apart from one another at a tool opening so as to form a socket between the to surface of the supporting means and the insertion means, wherein the insertion means forms a shape near the tool opening that tapers down to the insertion edge at two sides, and the insertion means and the supporting means bound the tool opening at the two sides; and
- access means in the supporting means for providing access to prepare the bone to accommodate the convex element, the supporting means fully surrounding the access means; and a cochlear implant system having the convex element.

* * * * *

UNITED STATES PATENT AND TRADEMARK OFFICE
CERTIFICATE OF CORRECTION

| | | |
|---|---|---|
| PATENT NO. | : 9,474,537 B2 | Page 1 of 1 |
| APPLICATION NO. | : 12/350550 | |
| DATED | : October 25, 2016 | |
| INVENTOR(S) | : Zimmerling et al. | |

It is certified that error appears in the above-identified patent and that said Letters Patent is hereby corrected as shown below:

In the Claims

In Column 6, Line 28:
replace "socket"
with --pocket--

In Column 6, Line 28:
replace "to"
with --top--

Signed and Sealed this
Third Day of January, 2017

Michelle K. Lee
*Director of the United States Patent and Trademark Office*